US009782527B2

(12) United States Patent
Thomas et al.

(10) Patent No.: US 9,782,527 B2
(45) Date of Patent: Oct. 10, 2017

(54) MONITORING OF REDUNDANT CONDUCTORS

(75) Inventors: Douglas C. Thomas, Carmichael, CA (US); David J. Burke, Concord, MA (US); Steven H. Reichenbach, Pleasanton, CA (US); Bryce A. Stammerjohan, San Francisco, CA (US); Thomas C. Rintoul, Gold River, CA (US)

(73) Assignee: TC1 LLC, St. Paul, MN (US)

( * ) Notice: Subject to any disclaimer, the term of this patent is extended or adjusted under 35 U.S.C. 154(b) by 440 days.

(21) Appl. No.: 12/472,812

(22) Filed: May 27, 2009

(65) Prior Publication Data
US 2010/0305692 A1   Dec. 2, 2010

(51) Int. Cl.
A61M 1/10    (2006.01)
A61M 1/12    (2006.01)
G01R 31/02   (2006.01)

(52) U.S. Cl.
CPC .............. *A61M 1/127* (2013.01); *A61M 1/10* (2013.01); *A61M 1/1086* (2013.01); *A61M 1/122* (2014.02); *G01R 31/024* (2013.01); *A61M 2205/16* (2013.01); *A61M 2205/18* (2013.01); *A61M 2205/702* (2013.01); *A61M 2205/8206* (2013.01); *A61M 2205/8262* (2013.01)

(58) Field of Classification Search
CPC . A61F 2013/8494; A61M 1/10; A61M 1/127; A61M 1/122; A61M 1/1086; G05B 9/03
USPC ......... 623/3.1, 3.27, 3.28, 912, 913; 600/16, 600/17; 361/93.7–93.9, 103, 87, 93.1; 324/500, 522; 417/44.11
See application file for complete search history.

(56) References Cited

U.S. PATENT DOCUMENTS

| 4,068,105 | A | * | 1/1978 | Jain et al. ..................... 324/500 |
| 4,227,145 | A | | 10/1980 | Bonikowski et al. |
| 4,888,011 | A | | 12/1989 | Kung et al. |
| 5,250,894 | A | | 10/1993 | Bridges et al. |
| 5,325,062 | A | | 6/1994 | Bachand et al. |
| 5,332,973 | A | * | 7/1994 | Brown et al. ................. 361/93.9 |
| 5,345,180 | A | * | 9/1994 | Maier et al. .................. 324/522 |
| 5,613,935 | A | | 3/1997 | Jarvik |
| 5,652,506 | A | | 7/1997 | Sorenson et al. |
| 5,713,954 | A | | 2/1998 | Rosenberg et al. |
| 5,725,357 | A | | 3/1998 | Nakazeki et al. |
| 5,733,313 | A | | 3/1998 | Barreras et al. |
| 5,894,273 | A | | 4/1999 | Meador et al. |

(Continued)

FOREIGN PATENT DOCUMENTS

JP    2006167142 A    6/2006
JP    A 2008-202974   9/2008

(Continued)

OTHER PUBLICATIONS

Okawa, description translation, JP 2006167142, pp. 1-15.*

(Continued)

*Primary Examiner* — Brian Pellegrino
(74) *Attorney, Agent, or Firm* — Kilpatrick Townsend & Stockton LLP

(57) ABSTRACT

This document relates to continuity monitoring of electrical conductors. For example, materials and methods for continuity monitoring of conductors for use providing power to a blood pump (e.g., an assist device) are provided.

28 Claims, 6 Drawing Sheets

(56) References Cited

U.S. PATENT DOCUMENTS

| | | | |
|---|---|---|---|
| 5,904,646 A * | 5/1999 | Jarvik | 623/3.27 |
| 5,947,703 A | 9/1999 | Nojiri et al. | |
| 5,947,892 A | 9/1999 | Benkowski et al. | |
| 6,137,416 A | 10/2000 | Meador | |
| 6,146,325 A | 11/2000 | Lewis et al. | |
| 6,149,683 A | 11/2000 | Lancisi et al. | |
| 6,227,797 B1 | 5/2001 | Watterson et al. | |
| 6,234,772 B1 | 5/2001 | Wampler et al. | |
| 6,264,601 B1 | 7/2001 | Jassawalla et al. | |
| 6,264,635 B1 | 7/2001 | Wampler et al. | |
| 6,278,251 B1 | 8/2001 | Schöb | |
| 6,468,041 B2 | 10/2002 | Ozaki | |
| 6,575,717 B2 | 6/2003 | Ozaki et al. | |
| 6,589,030 B2 | 7/2003 | Ozaki | |
| 6,605,032 B2 | 8/2003 | Benkowski et al. | |
| 6,626,644 B2 | 9/2003 | Ozaki | |
| 6,688,861 B2 | 2/2004 | Wampler | |
| 6,707,200 B2 | 3/2004 | Carroll et al. | |
| 6,736,770 B2 | 5/2004 | Leysieffer et al. | |
| 6,817,836 B2 | 11/2004 | Nose et al. | |
| 6,949,066 B2 | 9/2005 | Bearnson et al. | |
| 6,969,345 B2 | 11/2005 | Jassawalla et al. | |
| 7,138,776 B1 | 11/2006 | Gauthier et al. | |
| 7,150,711 B2 | 12/2006 | Nüsser et al. | |
| 7,229,474 B2 | 6/2007 | Hoffmann et al. | |
| 7,239,098 B2 | 7/2007 | Masino | |
| 7,284,956 B2 | 10/2007 | Nose et al. | |
| 7,462,019 B1 | 12/2008 | Allarie et al. | |
| 7,497,116 B2 | 3/2009 | Miyakoshi et al. | |
| 7,511,443 B2 | 3/2009 | Townsend et al. | |
| 7,563,225 B2 | 7/2009 | Sugiura | |
| 7,591,777 B2 | 9/2009 | Larose | |
| 7,645,225 B2 | 1/2010 | Medvedev et al. | |
| 7,699,588 B2 | 4/2010 | Mendler | |
| 7,854,631 B2 | 12/2010 | Townsendl et al. | |
| 7,861,582 B2 | 1/2011 | Miyakoshi et al. | |
| 7,887,479 B2 | 2/2011 | Larose et al. | |
| 7,951,062 B2 | 5/2011 | Morello | |
| 7,976,271 B2 | 7/2011 | LaRose et al. | |
| 8,157,720 B2 | 4/2012 | Marseille et al. | |
| 8,303,482 B2 | 11/2012 | Schima et al. | |
| 8,382,830 B2 | 2/2013 | Maher et al. | |
| 8,506,470 B2 | 8/2013 | Larose et al. | |
| 8,517,699 B2 | 8/2013 | Horvath | |
| 8,556,795 B2 | 10/2013 | Bolyard et al. | |
| 8,597,350 B2 | 12/2013 | Rudser et al. | |
| 8,764,621 B2 | 7/2014 | Badstibner et al. | |
| 8,870,739 B2 | 10/2014 | Larose et al. | |
| 8,882,477 B2 | 11/2014 | Fritz, IV et al. | |
| 8,956,275 B2 | 2/2015 | Bolyard et al. | |
| 2003/0069465 A1 | 4/2003 | Benkowski et al. | |
| 2007/0142696 A1 | 6/2007 | Crosby et al. | |
| 2007/0229295 A1 * | 10/2007 | Curt et al. | 340/653 |
| 2008/0319544 A1 | 12/2008 | Yaegashi | |
| 2010/0004761 A1 * | 1/2010 | Flanders et al. | 700/28 |
| 2010/0130809 A1 | 5/2010 | Morello | |
| 2010/0241223 A1 | 9/2010 | Lee et al. | |
| 2010/0327687 A1 | 12/2010 | Iannello et al. | |
| 2011/0071337 A1 | 3/2011 | Thompson et al. | |
| 2011/0237863 A1 | 9/2011 | Ricci et al. | |
| 2011/0313237 A1 | 12/2011 | Miyakoshi et al. | |
| 2012/0016178 A1 | 1/2012 | Woodard et al. | |
| 2012/0226097 A1 | 9/2012 | Smith et al. | |
| 2012/0245681 A1 | 9/2012 | Casas et al. | |
| 2013/0331934 A1 | 12/2013 | Kabir et al. | |
| 2014/0100413 A1 | 4/2014 | Casas et al. | |
| 2014/0194985 A1 | 7/2014 | Vadala, Jr. | |
| 2014/0275723 A1 | 9/2014 | Fritz, IV et al. | |
| 2014/0303426 A1 | 10/2014 | Kerkhoffs et al. | |
| 2014/0357937 A1 | 12/2014 | Reyes et al. | |
| 2015/0051438 A1 | 2/2015 | Taskin | |

FOREIGN PATENT DOCUMENTS

| | | |
|---|---|---|
| WO | WO9618358 A1 | 6/1996 |
| WO | WO9808564 A1 | 3/1998 |
| WO | 2008154387 | 12/2008 |

OTHER PUBLICATIONS

International Search Report & Written Opinion issued in Application No. PCT/US2010/036439, mailed Sep. 27, 2010, 19 pages.

PCT International Preliminary Report on Patentability for Application No. PCT/US2010/036439 mailed Dec. 8, 2011, 8 pages.

Canadian Office Action for Application No. 2,763,029 dated Dec. 19, 2012, 2 pages.

Japanese Office Action for Application No. 2012-513263, May 14, 2013, 1 page. (English translation).

Australian Examination Report No. 1 for Application No. 2010253836 dated Sep. 28, 2012, 3 pages.

JP2014-034767, Office Action, mailed Feb. 3, 2015, 5 pages.

JP2014-034767 , "Office Action", mailed Jun. 23, 2015, 2 pages.

* cited by examiner

MONITORING OF REDUNDANT CONDUCTORS

TECHNICAL FIELD

This document relates to continuity monitoring of electrical conductors. For example, this document provides monitors for blood pump systems as well as methods for monitoring continuity of redundant conductors providing power to a blood pump (e.g., an assist device).

BACKGROUND

Mechanical circulatory support (MCS) is a way of improving blood flow in a failing heart, using an electrically powered blood pump. A ventricular assist device (VAD) is a blood pump that works in conjunction with the recipient's own heart to pump sufficient blood throughout the body. Heart failure may affect the right side of the heart, limiting the ability of the heart to pump blood to the lungs, or the left side of the heart, resulting in an inability to pump sufficient oxygen-rich blood to the rest of the body. A VAD can provide short-term MCS support while a recipient is awaiting cardiac transplant or permanent MCS for a recipient who is not a candidate for transplantation, by delivering consistent blood flow to vital organs.

SUMMARY

This document relates to continuity monitoring of electrical conductors. For example, this document provides monitors for blood pump systems as well as methods for monitoring continuity of redundant conductors providing power to a blood pump (e.g., an assist device). In some cases, the methods provided herein can use a knowledge-based evaluation of the integrity of redundant conductors. For example, a monitor provided herein can determine continuity of redundant conductors by testing current in one conductor, comparing the current to a reference value, and determining whether the integrity of redundant conductor has been compromised based on a difference between a test value and a reference value. For example, a blood pump system provided herein can feature streamlined monitoring of redundant conductors for enhanced reliability.

In general, one aspect of this document features a blood pump system that comprises, or consists essentially of, a blood pump, a power supply, a conductor that carries electrical current between the power supply and the blood pump, one or more additional conductors that carry current between the power supply and the blood pump, and a first monitor configured to monitor the conductor and the one or more additional conductors for a failure condition. Monitoring the conductors includes detecting a first electrical current in the conductor and determining whether the failure condition occurred for at least one of the one or more additional conductors, based on the detected electrical current in the conductor. The blood pump system lacks a second monitor configured to detect a second electrical current in at least one of the one or more additional conductors.

The blood pump system can further comprise a controller configured to receive information from the first monitor about the first electrical current in the conductor. The controller can be configured to provide a signal to a user when a change in the first electrical current occurs in the conductor. The controller can be configured to provide information to a user about whether or not the conductor failed. The controller can be configured to provide information to a user about whether or not the one or more of the one or more additional conductors failed. The controller can include a feature for controlling pump speed. The controller can include a built-in rechargeable backup battery and a plurality of power or driveline connectors, which exit the system controller from the same side. The controller can include a visible LED indicator, a built-in LCD display, and a securing device.

In another aspect, this document features a method of monitoring the integrity of a conductor and one or more additional conductors. The conductor and the one or more additional conductors are included in a blood pump system, and the conductor and the one or more additional conductors carry electrical current. The method comprises, or consists essentially of, detecting a change in electrical current in the conductor without monitoring a change in electrical current in one or more of the one or more additional conductors; determining whether the integrity is compromised for at least one of the one or more additional conductors based on the detected electrical current in the conductor; and determining whether the integrity is compromised for the conductor based on the detected electrical current.

In another aspect, this document features a method for monitoring the integrity of a conductor and one or more additional conductors. The conductor and one or more additional conductors are part of a blood pump system and carry electrical current. The method comprises, or consists essentially of, determining a test electrical current in the conductor, while electrical current in one or more of the one or more additional conductors is not determined; comparing the determined test electrical current with a reference that indicates an electrical current that would be present in the conductor if the integrity of the conductor and the integrity of the one or more additional conductors were intact; determining whether the integrity is compromised for at least one of the one or more additional conductors based on the comparison of the determined test electrical current with the reference; and determining whether the integrity is compromised for the conductor based on the comparison of the determined test electrical current with the reference. The reference can comprise a reference electrical current detected in a reference conductor that is a redundant conductor configured to provide supplemental electrical current when the conductor, or at least one of the one or more additional conductors, has compromised integrity. The conductor, the reference conductor, and the one or more additional conductors carry current from a power supply to a blood pump included in the blood pump system. The conductor, the reference conductor, and the one or more additional conductors are configured such that each carries substantially the same electrical current under normal operation of the blood pump system.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the materials and methods are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document relates to continuity monitoring of electrical conductors. For example, this document provides monitors for blood pump systems as well as methods for monitoring continuity of redundant conductors providing power to a device such as a blood pump (e.g., an assist device). For example, a monitor provided herein can determine continuity of redundant conductors by testing current in one conductor, comparing the current to a reference value, and determining whether the integrity of a redundant conductor has been compromised.

The materials and methods described herein can provide continuity monitoring of conductors in any type of cord or cable. In some cases, an electrical cable can house an assembly of two or more conductors. A conductor can be any material that carries electric current. For example, a conductor can be a solid core electrical wire, or an assembly of fine stranded conductors. In some cases, a cable can house a pair of redundant conductors. In some cases, a cable can carry several pairs of redundant conductors. In some cases, a cable can house conductors to carry charge/discharge current, motor current, and other current necessary for operation of a device (e.g., a blood pump system). In some cases, a cable can house three or more groups of redundant conductors.

For example, the materials and methods provided herein can be used with conductors in a power cord that connects an electrically powered device to an electrical outlet, or a power cable that connects an electrically powered device to a battery. In some cases, an electrical cable can connect a VAD system controller to an external power source, such as a battery. In some cases, an electrical cable can be a percutaneous drive-line, connecting a VAD system controller to an implanted heart pump. In some cases, an electrical cable can connect an implanted heart pump directly to an external power supply.

Figure 1:
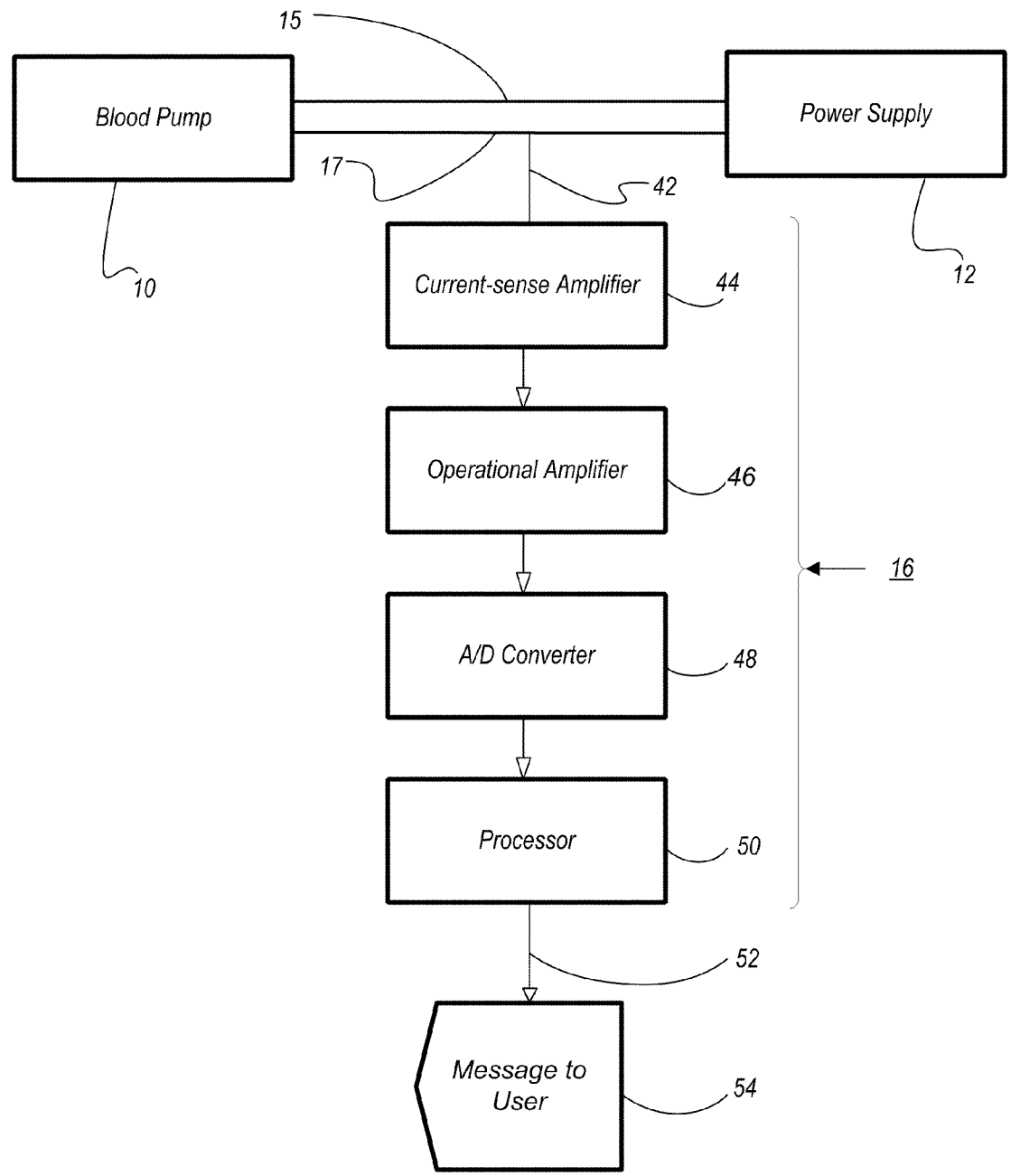
FIG. 1 is a schematic representation of an exemplary conductor continuity monitor.

Referring to FIG. 1, monitor 16 can be configured to monitor continuity of a pair of redundant conductors 15 and 17 carrying current between blood pump 10 and power supply 12. In some cases, monitor 16 can be configured to monitor continuity conductors carrying current between any two components of a blood pump system. For example, monitor 16 can monitor continuity of conductors between a blood pump and an external power supply, a blood pump and a system controller, or a system controller and a power supply.

Monitor 16 can be configured to detect conductor failure in a pair of redundant conductors by directly monitoring current carried by a single conductor (e.g., conductor 17) and not monitoring the current carried by another conductor in a group conductors (e.g., conductor 15). In some cases, monitor 16 can be configured to monitor a pair of redundant conductors by directly monitoring conductor 15 and not conductor 17. In some cases, monitor 16 can be configured to detect failure in conductors in systems using more than two redundant conductors to ensure system reliability. For example, monitor 16 can detect conductor failures in two, three, four, five, and six redundant conductors, by monitoring a single conductor of the group of conductors.

Conductors 15 and 17 can be a pair of redundant conductors. For example, conductor 15 can be a back-up conductor for conductor 17, and conductor 17 can be a back-up conductor for conductor 15. Conductors 15 and 17 can each carry a share of the electrical current flowing between system components. For example, conductors 15 and 17 can carry a substantially equal amount of current. In some cases, conductor 15 can carry about 50% of the electrical current between power supply 12 and pump 10, and conductor 17 can carry about 50% of the electrical current between power supply 12 and pump 10. In some cases, conductors 15 and 17 can each carry from about 100 mA to about 700 mA of current.

Any appropriate device can be used to monitor redundant conductors. For example, an appropriate monitor can be a device for measuring electrical current in and determining whether or not the current has increased or decreased. For example, a monitor can be a current transducer, or a semiconductor device that can detect a change in the magnitude of current carried by a conductor, and determine whether the change in current indicates conductor failure. For example, a monitor can be an integrated circuit or an array of integrated circuits. For example, a monitor can include analog signal conditioning and/or digital processing technology.

Monitor 16 can be configured to directly assess the integrity of conductor 17 and indirectly assess the integrity of conductor 15. For example, monitor 16 can be configured to detect a change in current carried by conductor 17, without directly detecting the change in conductor 15, to determine continuity of both conductors 15 and 17. For example, a monitor can detect no change in the magnitude of current carried by conductor 17, indicating that conductor 15 and conductor 17 are continuous conductors. In some cases, a monitor can detect an increase in the magnitude of current carried by conductor 17, indicating that conductor 15 has a discontinuity. In some cases, a monitor can detect a decrease in the magnitude of current in conductor 17, indicating that conductor 17 has a discontinuity. In yet other cases, using the substantially same approach and appropriate circuit logic that would be understood by a person of ordinary skill in the art, a short can also be detected in either of the conductors.

In some cases, a monitor can be configured to detect a change in current carried by conductor 15 and not conductor 17. For example, a monitor can detect no change in the magnitude of current carried by conductor 15, indicating that conductors 17 and 15 are continuous conductors. In some cases, a monitor can detect an increase in the magnitude of current carried by conductor 15, indicating that conductor 17 has a discontinuity. In some cases, a monitor can detect a decrease in the magnitude of current carried by conductor 15, indicating that conductor 15 has a discontinuity. Again, in yet other cases, using the substantially same approach and appropriate logic, a short to other conductors (or each other) or a short to ground can be detected.

A monitor can be configured to detect a change in current carried by a single conductor of a group of redundant conductors. For example, the integrity of a group of three, four, five, or six redundant conductors can be determined by directly monitoring the current flowing in a single conductor of a group. In some cases, a monitor can detect an increase in the magnitude of current flowing in a first conductor, indicating that one or more of a second, third, fourth, or fifth conductor can have a discontinuity.

Any appropriate method can be used to determine a change in the magnitude of current carried by a conductor. For example, the magnitude of current carried by a conductor can be compared to a reference value. The term "reference value" as used herein with respect to the magnitude of current is the current typically found in a fully operational conductor for an electrical device, without defect. For example, a reference value can be any appropriate value for a fully operational conductor, without defect, as determined at the time a device was manufactured, installed, or serviced. In some cases, an appropriate reference value can be determined before a device, such as a blood pump, is implanted. In other cases, the reference value can be determined in real time and/or by comparison to another current measurement. An example of the latter case is when the supply and return current to a load are measured. In the latter cases, this may permit the reference value to be determined based on differences in current consumption changes that may occur during different phases of the cardiac cycle and/or with patient condition (e.g., a VAD may need more current to provide more assistance for patients with weaker hearts). A decrease in the magnitude of current can be any detected value for the magnitude of current carried by a conductor, provided the value is less than a corresponding reference value. For example, a zero value for the magnitude of current carried by a conductor is a decrease in the magnitude of current carried by a conductor of a blood pump system.

An increase in the magnitude of current can be any detected value for the magnitude of current carried by a conductor, provided the value is greater than a corresponding reference value. For example, an increase in the magnitude of current carried by a conductor can be a value of about 1, 0.75, 0.67, 0.50, 0.33, or 0.25 times greater than the reference value. For example, in a pair of redundant conductors, a detected current can be up to about 2× a reference value, if an unmonitored conductor has failed.

With further reference to FIG. 1, monitor 16 can include current-sense amplifier 44 in one implementation. Appropriate current-sense amplifiers can detect the current as analog signal 42 from conductor 17 and condition (e.g., amplify, filter, etc.) the signal 42. Current-sense amplifier 44 can be an integrated circuit. Any appropriate current-sense amplifier can be used in monitor 16. For example, current-sense amplifier 44 can be a differential current-sense amplifier, a high-accuracy current-sense amplifier, a high-side current-sense amplifier, and a high voltage current-sense amplifier. Appropriate current-sense amplifiers for use in monitor 16 can be MAXIM™ high-side current-sense amplifiers, such as, MAX4173, MAX4173F, MAX4173H, and MAX4173T, high-side current-sense amplifiers.

In some implementations, the current-sense amplifier 44 includes a current sensor coupled with a signal-conditioning amplifier. The current sensor can be implemented using many techniques. For example, different current sensors include a voltage drop across an in-line resistor, a Hall sensor-based device, or a current transformer. The signal-conditioning amplifier can receive the detected current and condition it for later use. For example, the detected signal can be amplified so that current changes have greater absolute changes and are therefore easier to measure or conform to expected input for subsequent current detection circuitry.

Additionally, or alternatively, monitor 16 can include operational amplifier 46 in some implementations. For example, an appropriate operational amplifier can amplify small signals from current-sense amplifier 44. Operational amplifier 46 can be any appropriate operational amplifiers (e.g., an inverting amplifier, a non-inverting amplifier, a second-order low pass or high pass filter, or a single, dual or quad micropower operational amplifier). Examples of operational amplifiers include, without limitation MAXIM™ MAX4162, MAX4163, and MAX4164, operational amplifiers.

In some cases, monitor 16 can include analog-to-digital (A/D) converter 48. An appropriate A/D converter can be any device for converting analog signal 42 to discrete digital signals. For example, A/D converter 48 can be an integrated circuit. In some cases, a digital signal output can use coding schemes such as binary, Gray code or two's complement binary.

In some cases, monitor 16 can include digital signal processor 50. For example, an appropriate processor can decrypt digital signals from A/D converter 48, and convert the digital signals into information signal 52. For example, processor 50 can compare the magnitude of current detected to a reference value to determine whether the current detected in conductor 17 has increased, indicating a failure of conductor 15, or decreased, indicating a failure of conductor 17, or is unchanged, indicating continuity of conductors 17 and 15.

In some cases, informational signal 52 can be a signal communicating loss of current or conductor failure. In some cases, information signal 52 can be stored and/or communicated to user 54 via message. In some cases, a user can be a blood pump recipient, or a service technician. In some cases, information signal 52 can be transmitted to a system controller. For example, information signal 52 can be processed to trigger an audible alarm, a LED, or an icon on an LCD of a system controller to indicate conductor failure.

Figure 2:
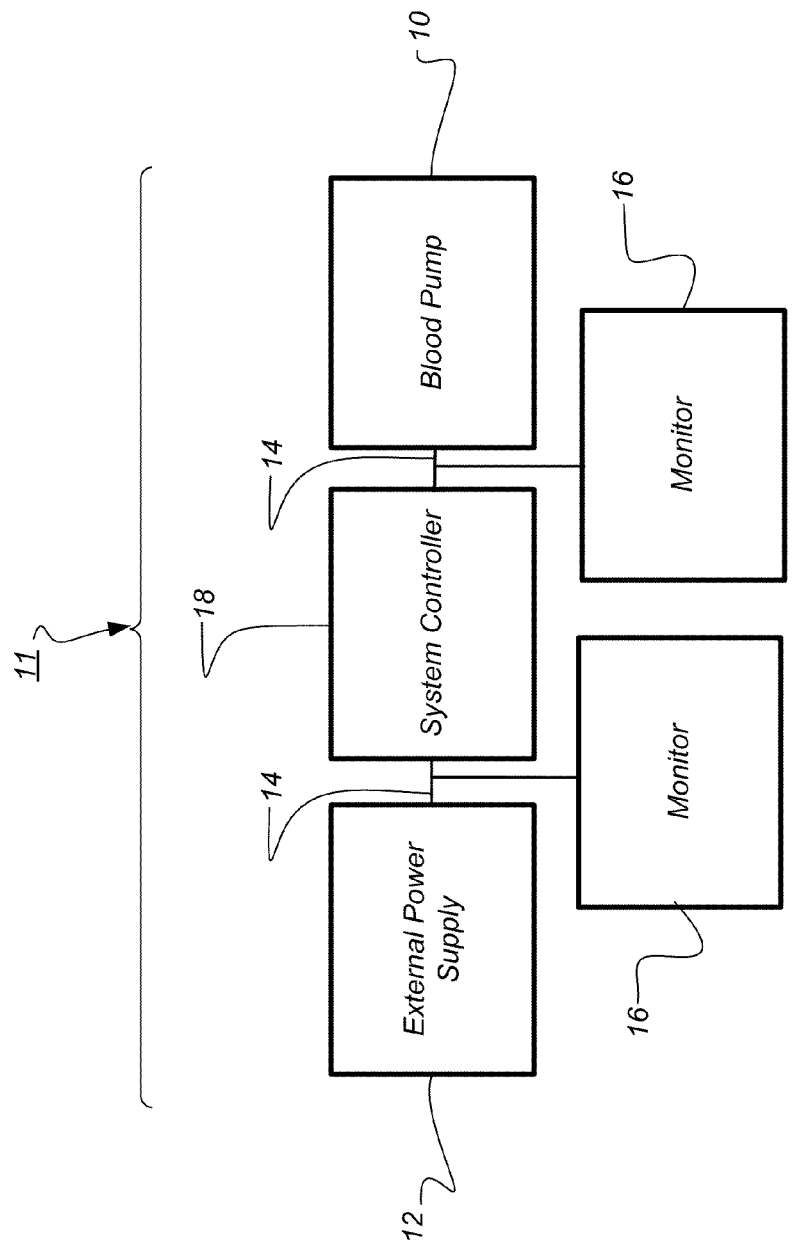
FIG. 2 is a schematic representation of a blood pump system.

Referring to FIG. 2, blood pump system 11 can include blood pump 10 and external power supply 12. In some cases, blood pump 10 can be connected to external power supply 12 by electrical cable 14. In some cases, blood pump system 11 can include monitor 16 to detect conductor failure in electrical cable 14. In some cases, blood pump system 11 can include more than one monitor 16. For example, blood pump system 11 can include a monitor for each group of redundant conductors. For example, if a cable connecting two components of a blood pump system houses three groups of redundant cables, a blood pump system can include an array of three monitors, which can be configured to detect a change in current carried by a single conductor of the group. For example, a blood pump system, having four groups of redundant conductors, with two, three, four, five or six conductors in each group (i.e., eight, twelve, sixteen, twenty, or twenty-four conductors in total), and can include four monitors.

In some cases, blood pump system 11 can include system controller 18. For example, system controller 18 can receive power from external power supply 12, and distribute power to blood pump 10 via system cables 14. In some cases, system controller 18 can receive signals from monitor 16 for conveying information regarding conductor failure to a blood pump recipient, or a service technician.

Any appropriate blood pump can be used with blood pump systems described herein. For example, an appropriate blood pump can be an electrically-driven pump for providing mechanical circulatory support. For example, external blood pumps (e.g., cardiac bypass devices) and implanted blood pumps (e.g., ventricular assist devices (VADs)) can be appropriate blood pumps.

Any appropriate source of power can be used in a blood pump system provided herein. For example, electrical outlets, external batteries, and implanted batteries, can be appropriate power supplies. External batteries can include a battery pack or packs. For example, a battery pack can carry at least two batteries. In some cases, a battery can be any type of battery required to provide power to a blood pump system. In some cases, a suitable battery can be a primary battery or a rechargeable battery.

Any appropriate cable can be used as a blood pump system cable. For example, an electrical cable or percutaneous cable can be used in a blood pump system described herein. In some cases, a cable can be permanently attached or releasably attached to a device. For example, some cables can feature connectors for releasable attachment to a device.

A blood pump system provided herein can include any appropriate device to command, direct or regulate the activity of components of a blood pump system (e.g., a system controller). In some cases, a system controller can house a monitor for detecting conductor discontinuity as described herein. In some cases, a system controller can house a monitor for each group of redundant conductors. For example, if a system cable included three groups of redundant conductors, a system controller can house an array of three monitors configured to detect a change in current in a single conductor of the group.

Figure 3A:
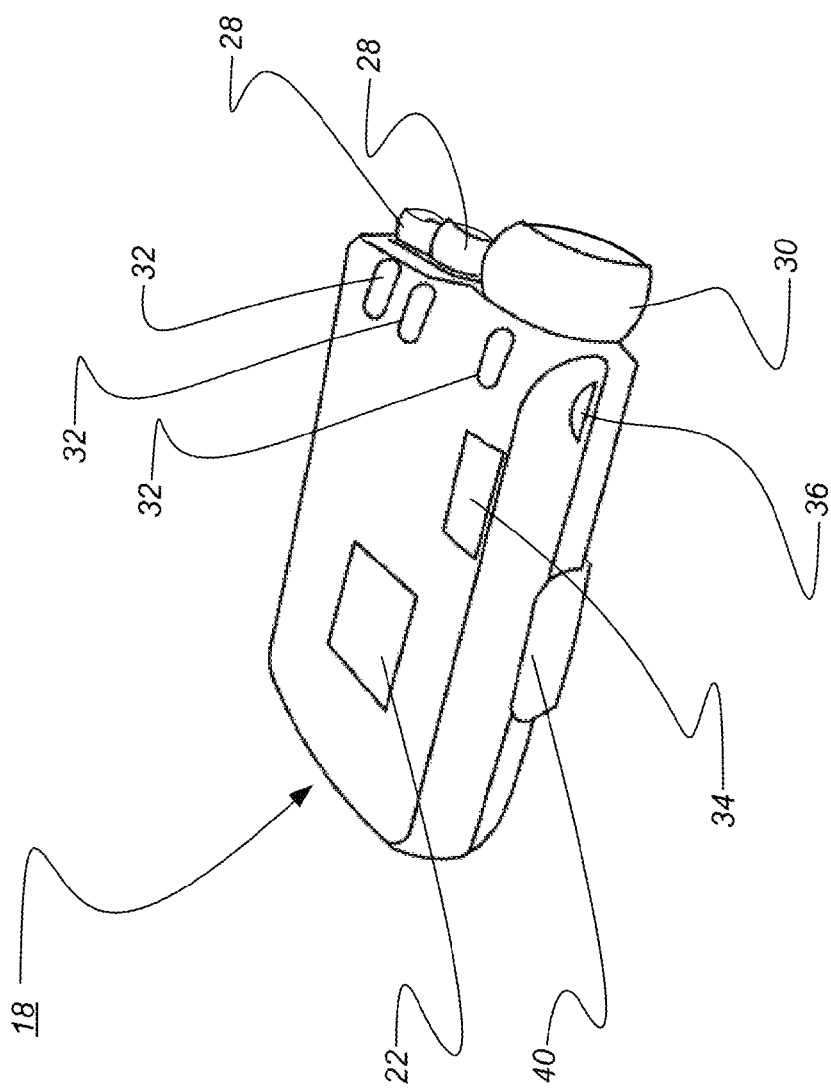
FIG. 3A is a perspective view of the front of an exemplary system controller.
Figure 3B:
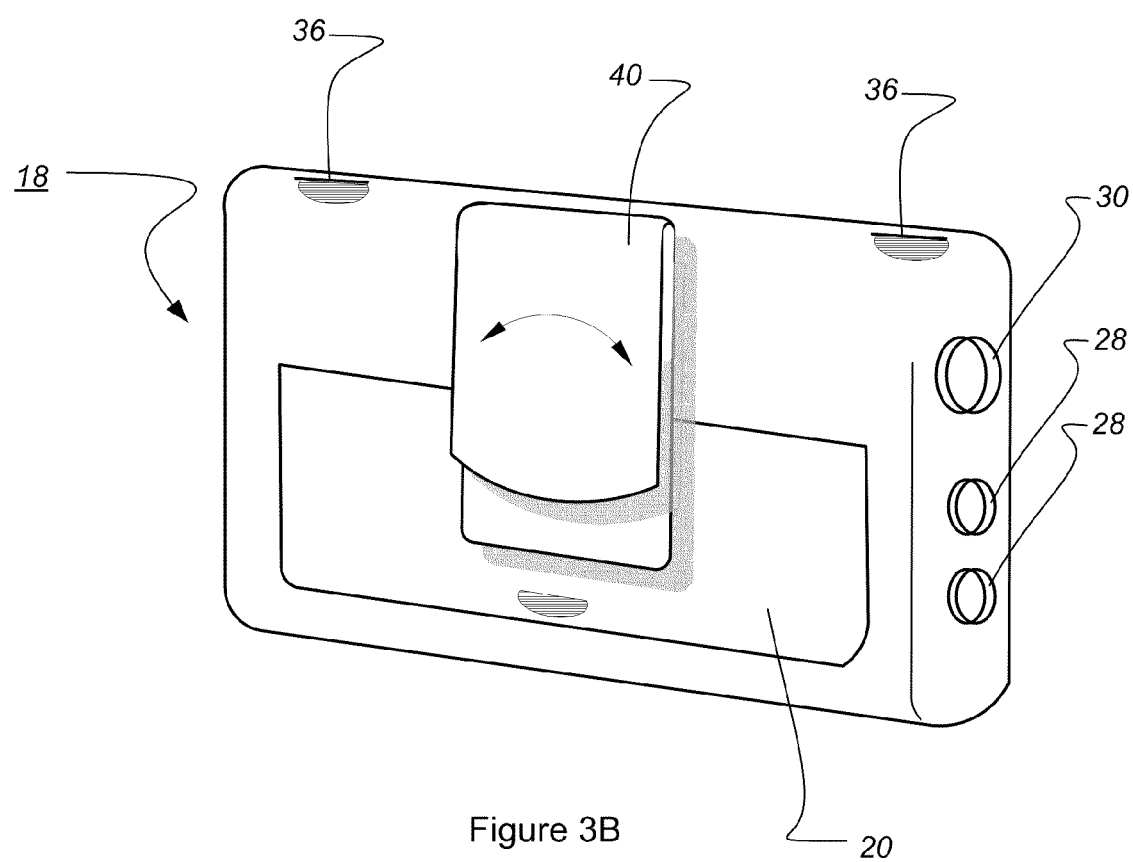
FIG. 3B is a perspective view of the back of an exemplary system controller.
Figure 3C:
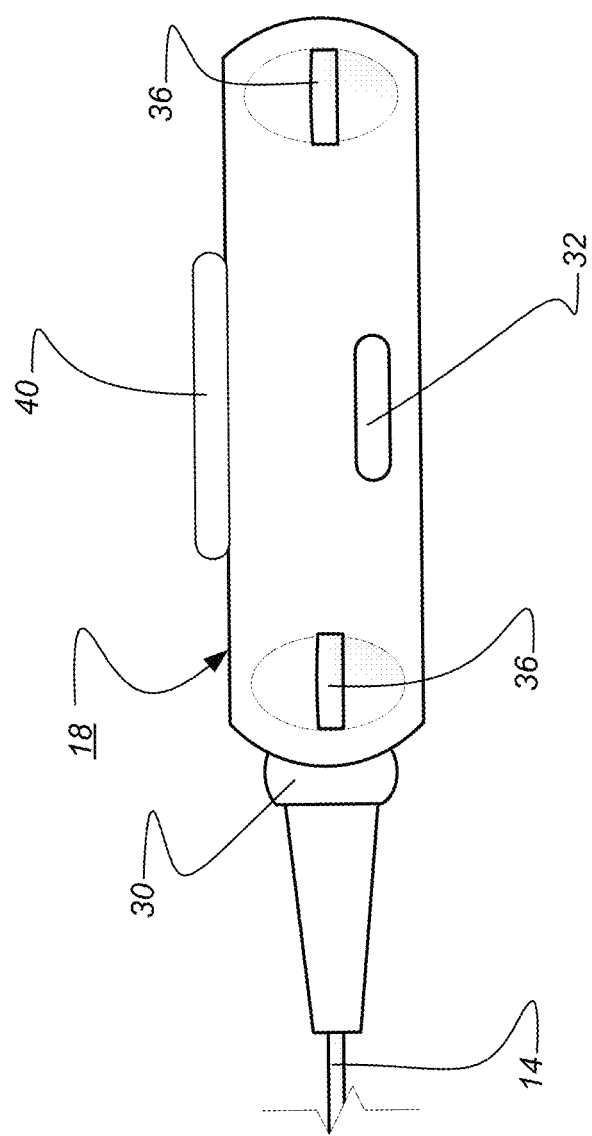
FIG. 3C is a top view of an exemplary system controller.

Referring to FIGS. 3A-3C, system controller 18 can be an external controller. In some cases, a controller can feature cable connectors 28 and 30. For example, system controller 18 can have cable connectors 28 for receiving power cables and a drive-line connector 30 for receiving a percutaneous lead. In some cases, connectors 28 and 30 can be on one side of system controller 18, and directed in a single direction. In some cases, connector 30 can include a safety mechanism to reduce the risk of accidental disconnection of a percutaneous lead. In some cases, system controller 18 can feature rounded corners for recipient comfort.

Referring to FIG. 3A, system controller 18 can include multiple components for communicating information regarding the status of a heart pump system to a recipient, a caregiver, or a service technician. For example, a system controller can include an audible alarm, integrated liquid crystal display (LCD) panel 22, and light emitting diode 32. In some cases, LED 32 and LCD panel 22 can communicate power connectivity, pump system status, and alarm history. In some cases, a system controller can include several LEDs. For example, one LED can communicate power connectivity, and another LED can communicate drive-line connectivity. In some cases, LED 32 and LCD panel 22 are located on the front face of system controller 18. In some cases, LED 32 and LCD panel 22 can be oriented so they can be read by a recipient looking downward.

System controller 18 can include control button 34 to access information provided through LCD panel 22. In some cases, a system controller can have up to three control buttons. For example, one button can be pressed to illuminate a battery gauge, and another button can silence an audible alarm. In some cases, simultaneous depression of multiple buttons, or prolonged depression of a single button can actuate hidden and semi-hidden features (e.g., features for setting pump parameters). For example, changing pump speed can be a hidden function accessed by a clinician, or accessed by a recipient with clinician assistance.

Any appropriate LCD screen can be included in a system controller described herein. For example, an appropriate LCD can enable patients and caregivers to attain data on power consumption, pump speed, flow, pulsatility index (i.e., quantification of the oscillations of the arterial blood-flow velocity waveform), pump and system status, and recent event history. In some cases, a LCD can support remote diagnosing. In some cases, data can be accessed through a LCD display by single button control. For example, to view speed setting, flow, pulsatility index, or power, a user can press a display control button, and cycle through read-outs for these data points.

Any appropriate LED can be included in a system controller described herein. In some cases, an LED can be a colored light (e.g., a red, yellow, or green light). In some cases, an appropriate LED can be designed for user-friendly communication (e.g., illuminating an icon). For example, an appropriate LED can provide information regarding battery status, routine maintenance needs, or system failures that require immediate service. In some cases, illumination of an icon can clarify a cause of an audible alarm (e.g., power loss or drive-line disconnection).

A system controller can include multi-sensory alarms. For example, icons, LEDs, auditory signals, and LCD display screen can provide primary and secondary levels of information to users. In some cases, LEDs and audible alarms can provide primary communication of status, alarms, and advisories. For example, red LEDs, in combination with a steady auditory tone, can be used to communicate urgency, and a need for immediate action and response. In some cases, advisories can be communicated through use of yellow LEDs and an audible intermittent tone. In some cases, a display screen can communicate secondary information about alarms, and status for non-routine events.

Referring to FIG. 3B, system controller 18 can include attachment site 36 for attaching a lanyard or other strap, and belt clip 40. In some cases, a system controller can include up to three attachment clips. In some cases, LED 32 (previously shown in FIG. 3A) can be placed on the top of system controller 18 so it can be seen by a recipient looking downward.

Referring to FIG. 3C, system controller 18 can include an internal back-up battery 20. In some cases, an appropriate back-up battery can be any battery that can operate a blood pump for 5-15 minutes in the event that cables for external power become disconnected from connectors 28. In some cases, a back-up battery can power an audible or visual signal (e.g., an alarm).

System controller 18 can include belt clip 40. A belt-clip can be any appropriate clip for securing a blood pump system controller to a belt worn by a recipient. In some cases, belt-clip 40 can be an articulating belt clip. In some cases, belt clip 40 can be a removable belt clip. In some cases, belt clip 40 can be capable of rotation. For example, belt clip 40 can capable of being rotated at least 180 degrees.

System controller 18 can include attachment site 36. An attachment site can be any part of the housing of a controller that can be secured to a strap or lanyard. Any appropriate strap or lanyard can be attached to an attachment site on a system controller. Appropriate straps can support a system controller and be worn or carried by a blood pump recipient. In some cases, a system controller can have several attachment sites.

Figure 4:
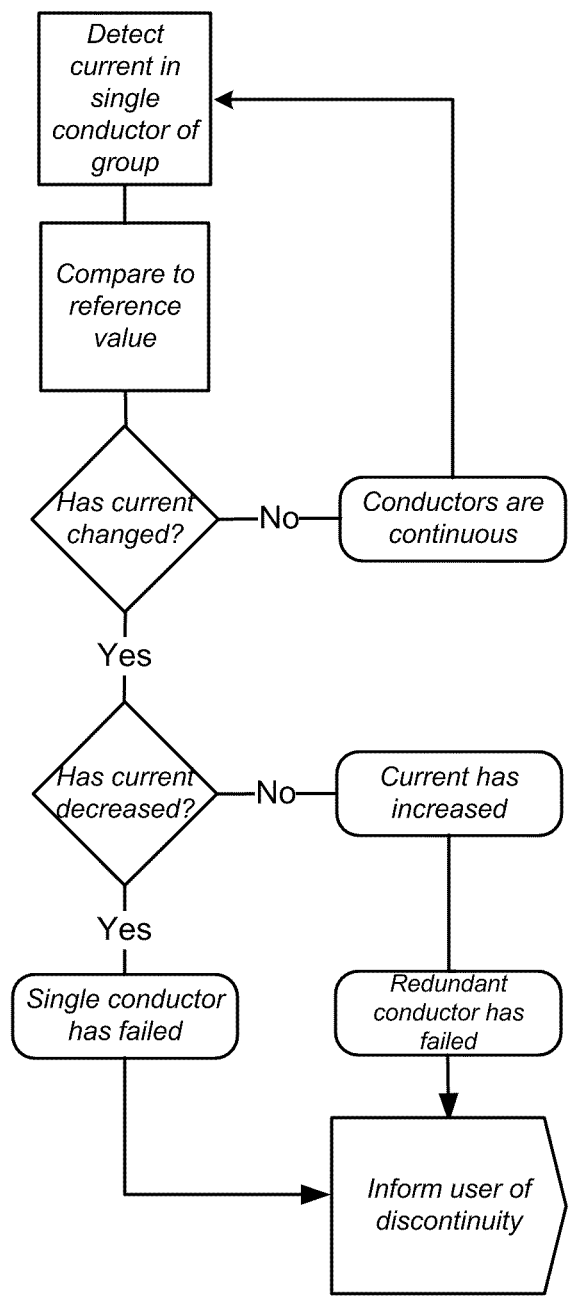
FIG. 4 is a flow chart of a method for monitoring continuity in redundant conductors.

This document also provides methods of monitoring the integrity of redundant conductors in a blood pump system. Referring to FIG. 4, methods provided herein can include detecting current flowing in a single conductor of a group of redundant conductors, for example, without detecting current in any other conductor of the group. In some cases, a method can include comparing a detected current to a reference value to determine whether there has been a change in the magnitude of current carried by a single conductor. In some implementations, the reference value is not a pre-set reference value, but a reference value that fluctuates based on the actual current consumption of the system. For example, the reference value may be based, or wholly derived from, one conductor's current. This reference conductor's current can be compared to a second conductor's current in real-time to determine whether the second conductor is operating as expected.

In some cases, a detected current can be less than a reference value. For example, if a conductor being directly monitored has failed, the detected current can be less than a reference value. In some cases, a detected current can be greater than a reference value. For example, if one or more indirectly monitored conductors has failed, the detected current in a directly monitored conductor can be greater than a reference value. In some cases, a detected current can be equal to a reference value. For example, if all conductors of a group are continuous, the detected current, in a single conductor being directly monitored, can be substantially equal to the reference value. In some cases, a method provided herein can include continuous monitoring. For example, if there is no change in the current of a conductor being directly monitored, a method can include re-detecting current in a single conductor, until a change is determined. In some cases, information about conductor discontinuity can be communicated to a blood pump user (e.g., a recipient or clinician).

As used herein, the term "monitoring integrity" refers to testing the current flowing in an electrical conductor and determining whether a conductor has been compromised. For example, compromised integrity can be discontinuity due to conductor failure, fracture, or wear. In some cases, compromised integrity can be intermittent, sporadic, or stable.

In some cases, monitoring integrity can refer to determining whether a monitored conductor is carrying excess current. For example, a conductor discontinuity can result in a monitored conductor carrying 0.5, 0.75, or 1 times more current than a conductor would carry if there were no discontinuity. As previously discussed, shorts also can be detected in an analogous fashion. In some cases, monitoring integrity can refer to determining whether a monitored conductor is carrying zero current.

Conductor integrity can be tested or assessed by any technique or device that can detect current and determine whether the current detected is greater than or less than a reference value. For example, the amount of current carried by a single conductor in a group of two or more conductors can be measured using a multimeter, current-sense transducer, or a series of integrated circuits (e.g., FIG. 1), and compared with a reference value. In some cases, a reference value can be the amount of current that would be present in a single conductor if the integrity of all conductors were intact.

A reference value can be a value from a previous test of conductor continuity. In some cases, a reference value can be a value determined when a device was manufactured, installed, or serviced. In some cases, a reference value for a medical device (e.g., a VAD) can be a test value detected at the time a device was surgically implanted in a recipient.

In other implementations, the reference value is obtained from a second monitored redundant pair. For instance, current consumption may change during different phases of the cardiac cycle and with patient condition. Thus, the reference value may need to change correspondingly during the cardiac cycle, for each patient, and for different times during the patient's use of the VAD (e.g., the current consumption may decrease if the patient's heart strengthens and is able to move more blood independently). Consequently, the reference value may change also. Obtaining the reference value from a second monitored redundant conductor that is also supplying current to the system provides a reference value that reflects the instant current needs of the system.

A reference value can be used to determine conductor integrity. For example, if a reference value is greater than a test value, the difference indicates a failure in a monitored conductor. In some cases, if a reference value is less than a test value, the difference can indicate a failure of one or more other conductors in a group of redundant conductors. For example, a pair of redundant conductors can carry between about 100 mA and 700 mA. In some cases, a reference value for a conductor of a pair of redundant conductors can be from 100 mA to about 400 mA. In some cases, a test value for a monitored conductor less than 100 mA can indicate a failure, or discontinuity in a monitored conductor. In some cases, a test value for a monitored conductor greater than 400 mA can indicate a failure in an unmonitored conductor.

The methods described herein can be used to monitor the integrity of redundant conductors. For example, a group of redundant conductors can be two or more conductors that share current load of a circuit. For example, each conductor in a pair of conductors can carry about 50% of the current load of a circuit. A group of redundant conductors can include two, three, four, or more conductors in a group of redundant conductors. For each group of redundant conductors, each conductor of a group can carry a substantially equal share of the current carried by the group. For example, a conductor of a group of three, four, five, or six redundant conductors can carry about 33%, 25%, 20%, or 17% of the current carried by a group of redundant conductors.

In some cases, information about conductor integrity can be provided to a user. For example, information about conductor continuity/discontinuity can be communicated to a blood pump recipient, a clinician, or a service technician. In some cases, information can be communicated through a system controller, via an audible or visual alarm. In some cases, information about conductor continuity can be stored in an event log in a system controller, and displayed on an LCD screen. In some cases, the information provided can display details about a discontinuity (e.g., whether the integrity of a monitored conductor or an unmonitored conductor has been compromised.)

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A blood pump system comprising:
a blood pump configured for implantation in a patient;
an external power supply configured to supply an electrical current to the blood pump for operation of the blood pump;
a percutaneous drive line including a first electrical conductor providing a first electrical current path between the external power supply and the blood pump and a second electrical conductor providing a second electrical current path between the external power supply and the blood pump, the second electrical current path being separated from and redundant to the first electrical current path over a redundant length of the percutaneous drive line such that, in the event of a discontinuity in one of the first and second current paths, the other of the first and second current paths will conduct an increased amount of the electrical current from the external power supply to the blood pump; and
a monitor including a current measuring device and a processing device, the current measuring device configured to measure electrical current in the first conductor and the processing device configured to monitor the electrical current in the first conductor and produce an information signal based on a comparison between the electrical current measured in the first conductor and a reference electrical current magnitude, the information signal indicating whether a discontinuity or a short occurred for the second conductor based on the comparison between the measured electrical current in the first conductor and the reference electrical current magnitude and not based on a measured current in the second conductor.

2. The blood pump system of claim 1, wherein:
the processing device is further configured to determine whether a discontinuity or a short occurred for the first conductor based on the comparison between the measured electrical current in the first conductor and the reference electrical current magnitude; and
the information signal is indicative of whether a discontinuity or a short occurred for the first conductor based on the comparison between the measured electrical current in the first conductor and the reference electrical current magnitude and not based on a measured current in the second conductor.

3. The blood pump system of claim 1, wherein:
the processing device is configured to assess a detected increase in the electrical current in the first conductor to detect a short in the first conductor; and
the processing device is configured to assess the detected increase in the electrical current in the first conductor to detect a discontinuity in the second conductor.

4. The blood pump system of claim 1, further comprising an additional monitor that monitors a reference conductor used to provide the reference electrical current magnitude to compare to the electrical current measured in the first conductor to determine if the electrical current measured in the first conductor has increased or decreased relative to the reference electrical current magnitude, wherein the reference conductor carries a reference electrical current having the reference current magnitude from the external power supply to the blood pump.

5. The blood pump system of claim 1, wherein the percutaneous drive line further comprising additional conductors that provide additional redundant current paths that carry electrical current between the external power supply and the blood pump, the first, second, and additional conductors being redundant conductors such that, in use, the first, second, and additional conductors each carry a share of the electrical current flowing from the external power supply to the blood pump.

6. The blood pump system of claim 1, wherein the first conductor and the second conductor are configured such that each carries substantially the same electrical current under normal operating conditions of the blood pump system.

7. The blood pump system of claim 1, wherein the blood pump comprises a ventricular assist device.

8. The blood pump system of claim 1, wherein the blood pump system further comprises a controller configured to receive information, from the monitor, about the measured electrical current in the first conductor.

9. The blood pump system of claim 8, wherein the controller is configured to provide a signal to a user when a change occurs in the measured electrical current in the first conductor.

10. The blood pump system of claim 9, wherein the controller is configured to provide information to a user about whether or not a discontinuity or a short occurred in the first conductor.

11. The blood pump system of claim 9, wherein the controller is configured to provide information to a user about whether or not a discontinuity or a short occurred in the second conductor.

12. The blood pump system of claim 9, wherein the controller comprises a feature for controlling pump speed.

13. The blood pump system of claim 9, wherein the controller comprises a built-in rechargeable backup battery and a plurality of power or driveline connectors, wherein each connector of said plurality exits the system controller from the same side.

14. The blood pump system of claim 13, wherein the built-in rechargeable backup battery is configured to provide power to the blood pump.

15. The blood pump system of claim 13, wherein the built-in rechargeable backup battery is configured to control a power alarm.

16. The blood pump system of claim 9, wherein the controller comprises a visible LED indicator, a built-in LCD display, and a securing device.

17. The blood pump system of claim 16, wherein the visible LED indicator indicates the status of power or driveline connectors of the controller.

18. The blood pump system of claim 16, wherein the built-in LCD display is configured to indicate a history of alarms or events.

19. The blood pump system of claim 16, wherein the built-in LCD display is configured to indicate a status of the pump.

20. The blood pump system of claim 16, wherein the built-in LCD display is configured to indicate modification of one or more pump parameters selected from a group consisting of pump speed, flow rate, power consumption, and pulsatility index.

21. The blood pump system of claim 16, wherein the securing device is selected from a group consisting of a lanyard, a belt clip, and a combination thereof.

22. The blood pump system of claim 21, wherein the belt clip is configured to be removable, articulating, or both.

23. The blood pump system of claim 1 further comprising a controller housing the monitor, the controller including a backup battery, three cable connectors on one side of the controller, and LED illuminated icons.

24. A method comprising:
transferring an electrical current from an external power supply to an implantable blood pump via a percutaneous drive line including a first electrical conductor providing a first electrical current path between the external power supply and the implantable blood pump and a second electrical conductor providing a second electrical current path between the external power supply and the implantable blood pump, the second electrical current path being separated from and redundant to the first electrical current path over a redundant length of the percutaneous drive line such that, in the event of a discontinuity in one of the first and second current paths, the other of the first and second current paths will conduct an increased amount of the electrical current from the external power supply to the implantable blood pump;
measuring electrical current flowing in the first electrical conductor;
generating, using at least one processing device, an information signal indicative of whether a discontinuity or a short occurred in the second electrical conductor based on the measured electrical current in the first electrical conductor and not based on a measured current in the second electrical conductor by comparing the measured electrical current in the first conductor with a reference electrical current magnitude; and
processing the information signal to trigger an audible and/or visual alarm in the event that the information signal indicates the occurrence of a discontinuity or short in the second electrical conductor.

25. The method of claim 24,
wherein the information signal is generated by the at least one processing device to be indicative of whether a discontinuity or a short occurred in the first conductor based on the comparison of the measured electrical current in the first conductor with the reference electrical current magnitude.

26. The method of claim 25, wherein the reference electrical current magnitude comprises an electrical current magnitude detected in a reference conductor that is a redundant conductor configured to provide supplemental electrical current from the external power supply to the implantable blood pump when a discontinuity or a short occurs in the first electrical conductor or the second electrical conductor.

27. The method of claim 26, wherein the implantable blood pump is included in a blood pump system.

28. The method of claim 26, wherein the first conductor, the reference conductor, and the second conductor are configured such that each carries substantially the same electrical current under normal operation of the implantable blood pump.

* * * * *